United States Patent [19]
Wetegrove et al.

[11] Patent Number: 6,023,070
[45] Date of Patent: Feb. 8, 2000

[54] SYSTEM AND METHOD TO MONITOR FOR FOULING

[75] Inventors: Robert L. Wetegrove, Winfield; Rodney H. Banks, Naperville, both of Ill.

[73] Assignee: Nalco Chemical Company, Naperville, Ill.

[21] Appl. No.: 09/055,134

[22] Filed: Apr. 3, 1998

[51] Int. Cl.[7] .................................................. G01N 5/00
[52] U.S. Cl. .......................... 250/573; 250/575; 73/61.62
[58] Field of Search .................................. 250/573, 574, 250/575, 301; 73/61.62; 165/11.1; 356/341, 440, 441, 442, 436

[56] References Cited

U.S. PATENT DOCUMENTS

| | | | |
|---|---|---|---|
| 2,719,427 | 10/1955 | McKeown | 73/61.62 |
| 3,731,091 | 5/1973 | Rosso et al. | 250/301 |
| 4,015,134 | 3/1977 | Sturm | 250/565 |
| 4,105,334 | 8/1978 | Halko et al. | 356/339 |
| 4,896,047 | 1/1990 | Weaver et al. | 250/573 |
| 5,185,533 | 2/1993 | Banks et al. | 250/575 |
| 5,488,856 | 2/1996 | Dirk | 73/61.62 |

*Primary Examiner*—Edward P. Westin
*Assistant Examiner*—Thanh X. Luu
*Attorney, Agent, or Firm*—Hill & Simpson

[57] ABSTRACT

A system and a method for monitoring fouling in a fluid stream are provided. A light source generates a light path directed to two distinct portions of a fluid stream, one of which includes a translucent conduit. The conduit experiences fouling on the walls thereof. The light directed towards the conduit is absorbed or scattered to a varying degree as a function of foulant thickness and composition and the wavelength of the light employed. A comparison of foulant contained in the fluid itself may be compared to the foulant in the conduit, and a signal representative thereof can be generated. As a result, dosage of agents added to the fluid stream to control the foulant in the system may be controlled.

20 Claims, 3 Drawing Sheets

SYSTEM AND METHOD TO MONITOR FOR FOULING

BACKGROUND OF THE INVENTION

The present invention generally relates to a system and method for monitoring a fluid in a fluid-containing system. More specifically, the present invention relates to a monitoring device and method for monitoring surface fouling in fluid-containing systems.

It is, of course, generally known to provide a fluid system in which fluid is transported from one location to another location. One such example is a water cooling tower in which heat exchange tubing is provided for transport of water from a first location to a second location. In such a system, unwanted film or fouling is often created on internal surfaces of the tubing. The film is typically due to microorganisms or colored or particulate matter suspended in the water flowing in the system. The film typically grows in thickness reducing the efficiency of, for example, heat transfer from a hot interior to a cooler ambient environment.

Of course, many other systems that implement fluid transfer are known. For example, although the fluid may be water, it could be natural gas in a transmission line. The film may be caused by any material in the fluid strain whether biological or even inorganic trapped in the fluid.

One film fouling monitoring device is taught and described in U.S. Pat. No. 5,185,533 to Banks et al. In the '533 patent, a system is provided for determining accumulative film thickness at the inside diameter of a main stream conduit conducting a main stream of a flowing fluid by using a transparent shunt conduit to shunt from the main stream a sample stream of the process fluid. A reference light emitter and light detector at a referenced section of the shunt is provided wherein any appreciable film is removed. An upstream sample light emitter and detector are opposed thereto wherein any film is allowed to form. A common source of light is provided so that respective emitters emit light beams of the same intensity. Means for determining concurrently intensities of light received by the detectors whereby film thickness may be determined for the sample is also provided.

Accordingly, Banks et al. teach a device which uses two light paths from a single light source. Both light paths go through a transparent tube although one of the beams goes through a section of the tube kept free of deposits by a mechanical wiper. This clean section reading allows the reading from the fouled section of the tubing to be corrected for any effects of color or turbidity in the water. This device, however, is rather expensive given the cost of the mechanical wiper assembly. In addition, such a wiper assembly, being mechanical in nature, can be unreliable.

A need, therefore, exists for a less complex and less costly system and method for monitoring for fouling in a fluid stream that is both reliable and inexpensive. As a result, control and optimized feeding of antifouling and biocidal treatments may be added to the system following monitoring.

SUMMARY OF THE INVENTION

A system and a method for monitoring fluid in a fluid path of a system is provided. The system and the method may be employed in any type of fluid treatment systems wherein the fluid in the system carries particulate matter often causing fouling or the like. In addition, the present invention may be implemented to monitor fluorescence associated with biological or chemical substance on the walls of a tube or in a fluid phase.

To this end, in an embodiment of the present invention, a system is provided for monitoring of fouling. The system has a light source emitting light in a light path. A fluid conduit has walls of a finite length defining an interior through which a fluid passes wherein the walls allow the light to pass therethrough wherein the fluid includes material causing fouling on the walls. A discharge area is provided outside the finite length of the fluid conduit wherein the light passes through only the fluid discharged from the fluid conduit at the discharge area. A detector receives transmitted light through the fluid conduit and produces a signal representative thereof. Means is provided for processing the signal and producing a signal indicative of an amount of fouling present.

In an embodiment, a shield surrounds the fluid conduit and the discharge area.

In an embodiment, a second detector receives transmitted light through the discharge area and produces a signal representative thereof.

In an embodiment, the light source emits light in two light paths.

In an embodiment, means is provided for re-directing the light in the light path to produce a second light path.

In an embodiment, alarm means is connected to the means for processing and activated upon reaching a predetermined level of fouling.

In an embodiment, a controller adds a treatment agent to the fluid based on the signal received from the means for processing.

In another embodiment of the present invention, a fouling monitoring system is provided. The system has a fluid stream and a conduit having a finite length defined by walls through which the fluid stream passes. A discharge area is provided beyond the finite length of the conduit wherein the fluid stream enters the discharge area after passing through the conduit. Light emitting means creates a light path to radiate through the fluid stream in the conduit and the fluid stream in the discharge area. A first detector receives transmitted light that radiates through the fluid stream flowing through the conduit and produces a first signal representative thereof. A second detector receives transmitted light that radiates through the fluid stream in the discharge area and produces a second signal representative thereof. A processor receives the first signal and the second signal and calculates an amount of fouling based on the signals.

In an embodiment, a control means is responsive to the amount of fouling to add a treatment agent to the fluid stream upon reaching a predetermined level.

In an embodiment, an alarm means provides a signal indicative of the amount of fouling reaching a predetermined level.

In an embodiment, reflection means in the light path creates two light paths.

In an embodiment, a light shield surrounds the conduit and the discharge area.

In an embodiment, the conduit is translucent.

In another embodiment of the present invention, a method is provided for monitoring for fouling in a system. The method comprises the steps of: providing a fluid path directed through a finite length of conduit and discharged in an area beyond the finite length of conduit; emitting light through the fluid path at the finite length of conduit and at the area beyond the finite length of tubing; detecting an amount of light that passes through the finite length of conduit and the area beyond the finite length of tubing;

producing a first signal representative of the amount of light that passes through the finite length of conduit; producing a second signal representative of the amount of light that passes through the area beyond the finite length of conduit; and comparing the first signal and the second signal to determine an amount of fouling in the system.

In an embodiment, a controlled amount of a treatment agent is added to the fluid path.

In an embodiment, ambient light is shielded from the finite length of conduit and the area beyond the finite length of tubing.

In an embodiment, light is reflected to produce a plurality of light paths.

In an embodiment, the finite length of conduit includes translucent walls.

In an embodiment, an alarm provides an indication of the amount of fouling reaching a predetermined level.

In an embodiment, the fluid is water including particulate materials suspended in the water.

It is, therefore, an advantage of the present invention to provide a system and a method for monitoring for fouling in a fluid treatment system.

Yet another advantage of the present invention is to provide a system and a method for monitoring fouling that is inexpensive to implement.

Moreover, an advantage of the present invention is to provide a system and a method for monitoring fouling that is reliable in operation.

A still further advantage of the present invention is to provide a system and a method for monitoring fouling that also incorporates feeding control of antifouling agents, for example.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides a system and a method for monitoring a fluid stream for fouling. More specifically, surface fouling in fluid-containing systems may be monitored and controlled by the system and method of the present invention.

Figure 1:
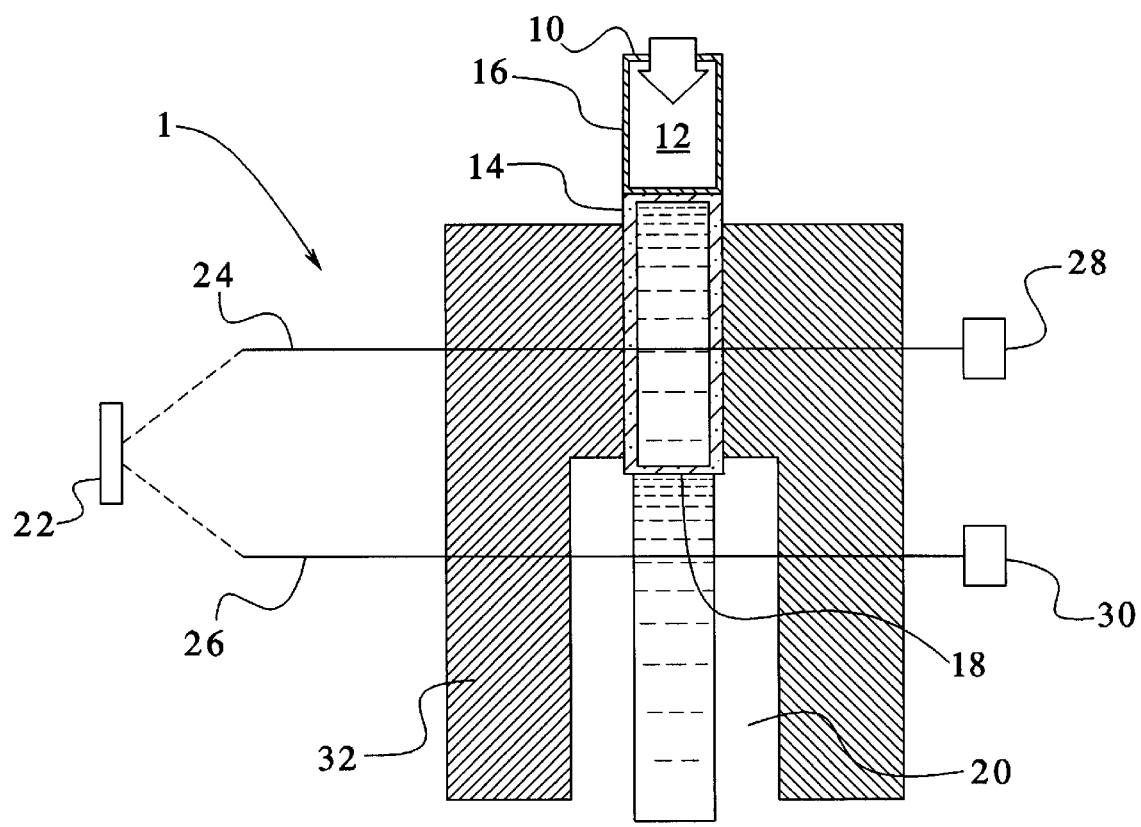
FIG. 1 illustrates a schematic view of an embodiment of a system for monitoring fluids.

Referring now to FIG. 1, a first embodiment of a system 1 for monitoring fouling of the present invention is shown. The system 1 is implemented for monitoring for fouling that may occur on walls of a conduit in the system 1. To this end, water or other like fluids flow into the system 1 at an input 10. The fluid 12 flows or is pumped into the input 10 of the system 1. Translucent conduit 14 is provided in a location or section intermediate a pipe 16 including the input 10. The pipe 16 and the conduit 14 are in fluid communication and may be integrally formed. The conduit 14 preferably includes translucent walls such that light may be emitted through the walls of the conduit 14. The conduit 14 is of a finite length and terminates at an output 18 such that the fluid 12 enters a discharge area 20. The discharge area 20 is a section in which the fluid is not contained or directed by the pipe 16 or the conduit 14.

Without incorporating or using anti-fouling methods for treatment, the walls of the conduit 14 typically experience fouling. The resultant fouling absorbs or scatters light to varying degrees as a function of fouling thickness and composition and the wavelength of the light used. Fouling occurs mainly as a result of slime-producing microorganisms, deposition of oils and grease, and entrapment of particulates, flowing in the fluid 12 and collecting on the walls of, for example, the pipe 16 or the conduit 14.

Fluid in the discharge area does not exhibit fouling due to lack of a conduit and, therefore only the properties of the fluid itself are measured and can be used to correct for color and turbidity of the fluid stream.

To monitor and to control fouling, the system 1 of the present invention incorporates a light source 22 that emits light in a first light path 24 and a second light path 26. The first light path 24 is directed so that light is emitted through the translucent conduit 14 and alternately received by a detector 28. Similarly, the light path 26 is directed through the fluid that has exited the output 18 of the conduit 14 in the discharge area 20. The light path 26 after passing through the fluid 12 in the discharge area 20 is received by a detector 30. As mentioned, fouling results in absorbance or scattering of light in the light path 24 to a varying degree. In addition, light is absorbed by colored or particulate materials suspended in the flowing fluid 12. To prevent extraneous light from affecting the system 1, a shield 32 may be incorporated. The shield 32 has paths to allow the light paths 24 and 36 to pass through, however, the shield 32 and through the conduit 14 and the discharge area 20. However, extraneous light is substantially prevented from entering these areas to prevent erroneous readings by the detectors 28,30. In addition, the present invention provides a means to electronically exclude effects due to extraneous light. To this end, circuitry using an integrated circuit, for example, AD630 by Analog Devices, provides lock-in detection and amplification of the light passing through the fluid in the conduit and discharge area.

Under certain environmental conditions, condensation of water vapor on the optical components may occur giving erroneous results in degree of fouling. This effect may be minimized by maintaining the optical components at a temperature equal to or greater than the temperature of the water stream. This may be achieved by several methods, of which the following are illustrative, but not limiting, examples: electrical resistance heating of the optical elements, irradiation of the optical elements with a wavelength of light not interfering with the optical measurements, passing the sample stream in a conduit or chamber surrounding and thus adjusting the temperature of the optical components of the monitor. Additionally, condensation may be controlled by directing a stream of warm and/or dry air across the optical elements in the measurement chamber.

Ordinarily, however, light absorbance may not be differentiated between surface fouling and light absorbance from materials in the water stream. However, by implementing the system 1 of the present invention, using the light path 26 passing through the fluid 12 in the discharge area 20, but not through the area including the fouled surface defined by the location of the conduit 14, a comparison of intensities of the detected light at the detector 30 with the light at the detector 28 may be performed. In addition, compensation for light absorbance due to the fluid stream alone may be accounted for by detecting light at each of the locations. This compensation is accomplished by calculating the degree of fouling as an absorbance:

$$\text{absorbance} = \log\left[\frac{\text{Intensity of light through discharge area}}{\text{Intensity of light through conduit}}\right]$$

As will be explained with reference to FIG. 3, electronic components may be incorporated into the system 1 to manage the power supply, light output, light detection, signal processing, data acquisition, processing, and storage. In addition, communication with other devices may also be provided to, for example, signal alarms or activate corrective actions for the process being monitored, such as control of an additive or treatment agent to optimize feed of anti-fouling and/or biocidal treatment to the fluid stream.

Figure 2:
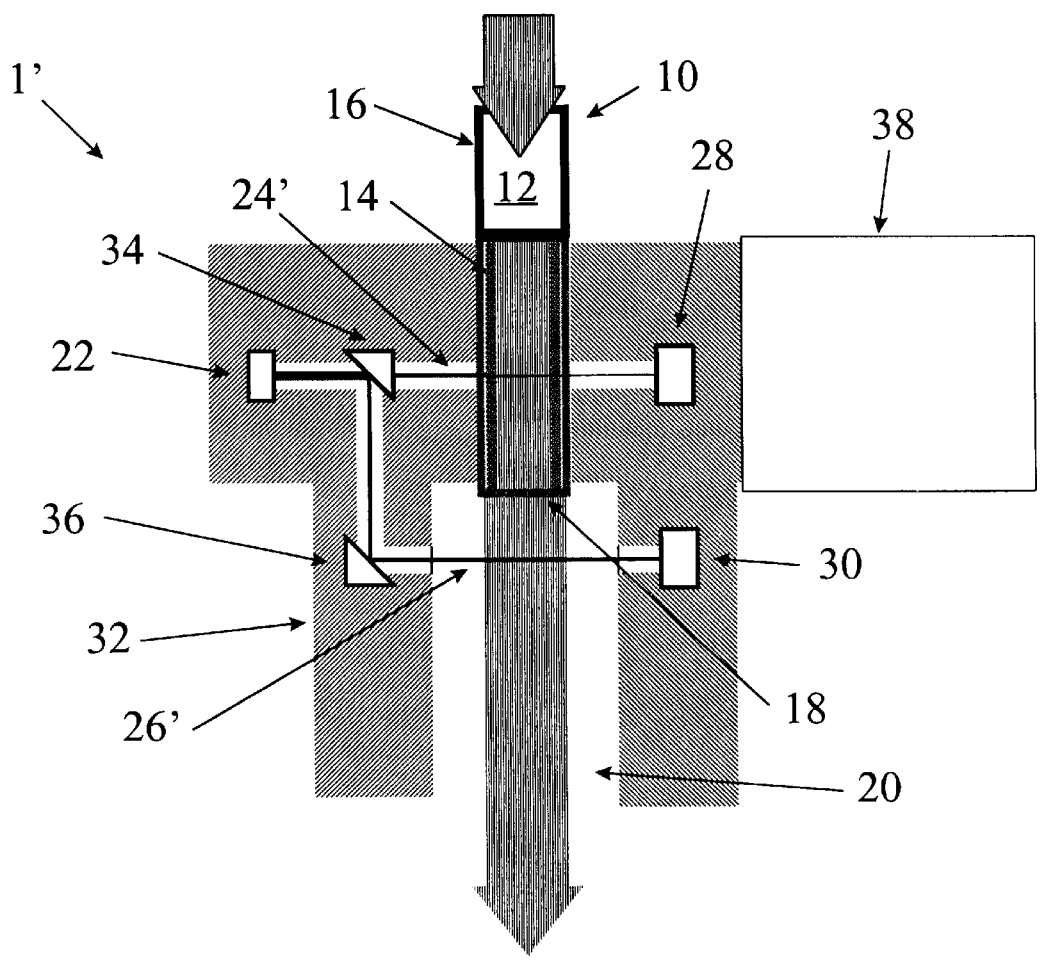
FIG. 2 illustrates a schematic view of an alternate embodiment of a system for monitoring fluids.

Referring now to FIG. 2, an alternate embodiment of the system 1 of the present invention shown in FIG. 1 is illustrated. In FIG. 2, like numerals refer to like parts. The primary distinction in FIG. 2 is the incorporation of a half mirror 34 and a mirror 36 situated between the light source 22 and the fluid 12 within the system 1'. The half mirror 34 allows light to pass through a section of the half mirror 34 and through the conduit 14 and, hence, the fluid 12 flowing through the conduit 14. In addition, the half mirror 34 redirects a portion of the light path to the mirror 36 which re-directs the light path 26' through the discharge area 20 including the fluid 12 and to the detector 30. Likewise, low-voltage electronics are provided as generally shown by the box designated 38.

Figure 3:
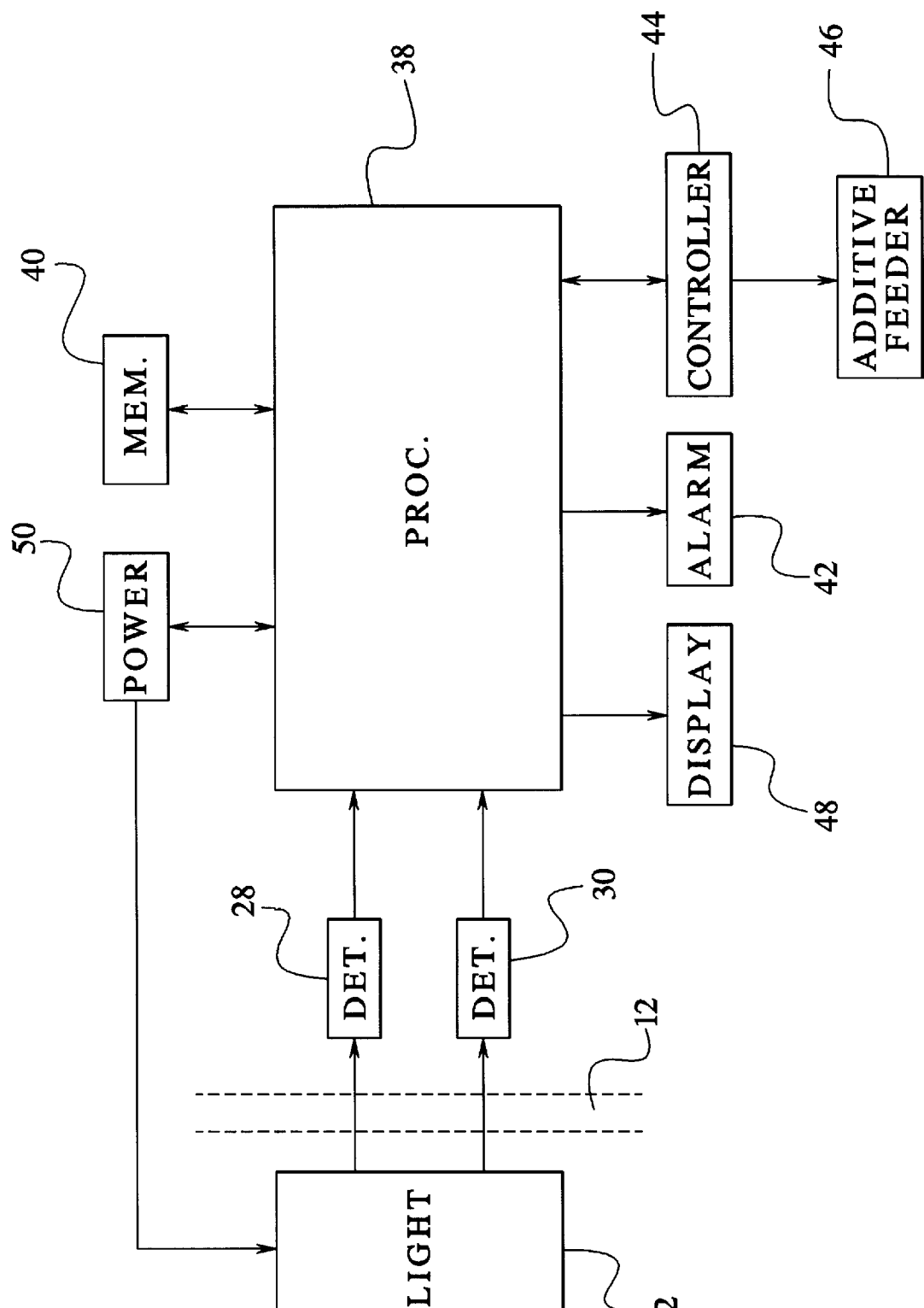
FIG. 3 illustrates a black box diagram of a system for monitoring fouling in a fluid system.

Referring now to FIG. 3, a black box diagram of a system for implementing the present invention is generally illustrated. As shown, the light source 22 is provided which generates one or more light paths to be transmitted through a fluid stream shown in phantom at numeral 12 in FIG. 3. Detectors 28,30 detect the amount of light passing through the fluid stream 12 and generate a signal indicative thereof. The signals are sent to a processor 38.

The processor 38 uses the detected signals forwarded by the detectors 28,30 and provides an indication as to the amount of fouling in the system as described earlier. The processor 38 may be provided with memory 40 which may store data indicative of predetermined levels of fouling that may be harmful to the system or which require additives to treat the fluid stream. If such predetermined levels are reached, an alarm 42 may be provided and may be activated upon reaching or exceeding certain predetermined levels. The alarm 42 may be visual or audio in nature or a combination of both.

Likewise, if the same or other predetermined levels are reached or exceeded, the processor 38 may provide a signal to a controller 44. The controller 44, among other things, may control the addition of additives to the process stream 12 via an additive feeder 46. Further, a display 48 may be provided for real time and continuous monitoring of the system. The display receives signals from the processor 38 that may indicate the amount of fouling, the rate of change in fluid stream fouling, or the like. In addition, the display 48 may provide information in real time regarding the addition of additives added to the fluid stream as well as the effect of those additives to the fluid stream.

The system may be powered by a power source 50 to provide power to the processor 38 as well as the light source 22. The present invention may also be implemented using other light sources and detectors such that the specific design could be used to monitor, for example, fluorescence associated with biological or chemical substances of the walls of a tube or in a fluid phase.

As a result of the system and method of the present invention, a low cost, highly reliable system for monitoring fouling and effecting feeding of antifouling and biocidal treatments is provided. As a result, control and optimization of feed and monitoring of foulant can be effectively provided.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. A system for monitoring for fouling, the system comprising:
   a light source emitting light in a light path;
   a fluid conduit having walls of a finite length defining an interior through which a fluid passes wherein the walls allow the light to pass therethrough wherein the fluid includes material causing fouling on the walls;
   a discharge area outside the finite length of the fluid conduit wherein the light passes through the fluid discharging from the fluid conduit at the discharge area;
   a detector receiving transmitted light through the fluid conduit and producing a signal representative thereof; and
   means for processing the signal and producing a signal indicative of an amount of fouling present.

2. The system of claim 1 further comprising:
   a shield surrounding the fluid conduit and the discharge area.

3. The system of claim 1 further comprising:
   a second detector receiving transmitted light through the discharge area and producing a signal representative thereof.

4. The system of claim 1 wherein the light source emits light in two light paths.

5. The system of claim 1 further comprising:
   means for re-directing the light in the light path to produce a second light path.

6. The system of claim 1 further comprising:
   alarm means connected to the means for processing and activated upon reaching a predetermined level of fouling.

7. The system of claim 1 further comprising:
   a controller for adding a treatment agent to the fluid based on the signal received from the means for processing.

8. A fouling monitoring system comprising:
   a fluid stream;
   conduit having a finite length defined by walls through which the fluid stream passes;
   a discharge area beyond the finite length of the conduit wherein the fluid stream enters the discharge area after passing through the conduit;
   light emitting means creating a light path to radiate through the fluid stream in the conduit and the fluid stream in the discharge area;
   a first detector receiving transmitted light that radiates through the fluid stream flowing through the conduit and producing a first signal representative thereof;

a second detector receiving transmitted light that radiates through the fluid stream in the discharge area and producing a second signal representative thereof; and a processor receiving the first signal and the second signal and calculating an amount of fouling based on the signals.

9. The system of claim 8 further comprising:

a control means responsive to the amount of fouling to add a treatment agent to the fluid stream upon reaching a predetermined level.

10. The system of claim 8 further comprising:

an alarm means providing a signal indicative of the amount of fouling reaching a predetermined level.

11. The system of claim 8 further comprising:

reflection means in the light path creating two light paths.

12. The system of claim 8 further comprising:

a light shield surrounding the conduit and the discharge area.

13. The system of claim 8 wherein the conduit is translucent.

14. A method for monitoring for fouling in a system, the method comprising the steps of:

providing a fluid path directed through a finite length of conduit and discharged in an area beyond the finite length of conduit;

emitting light through the fluid path at the finite length of conduit and at the area beyond the finite length of tubing;

detecting an amount of light that passes through the finite length of conduit and the area beyond the finite length of tubing;

producing a first signal representative of the amount of light that passes through the finite length of conduit;

producing a second signal representative of the amount of light that passes through the area beyond the finite length of conduit; and comparing the first signal and the second signal to determine an amount of fouling in the system.

15. The method of claim 14 further comprising the step of:

controlling an amount of a treatment agent to be added to the fluid path.

16. The method of claim 14 further comprising the step of:

shielding ambient light from the finite length of conduit and the area beyond the finite length of tubing.

17. The method of claim 14 further comprising the step of:

reflecting the light to produce a plurality of light paths.

18. The method of claim 14 wherein the finite length of conduit includes translucent walls.

19. The method of claim 14 further comprising the step of:

providing an alarm indicative of the amount of fouling reaching a predetermined level.

20. The method of claim 14 wherein the fluid is water including particulate materials suspended in the water.

* * * * *